United States Patent [19]

Mizutani et al.

[11] 4,327,094
[45] Apr. 27, 1982

[54] INSECTICIDAL AND ACARICIDAL 3,5-DIOXO-2,3,4,5-TRIAZINE COMPOUNDS

[75] Inventors: Masato Mizutani, Kyoto; Kazunori Tsushima, Nishinomiya; Yuzuru Sanemitsu, Ashiya; Masachika Hirano, Ibaraki, all of Japan

[73] Assignee: Sumitomo Chemical Company, Limited, Osaka, Japan

[21] Appl. No.: 225,749

[22] Filed: Jan. 16, 1981

[30] Foreign Application Priority Data

Jan. 29, 1980 [JP] Japan .................................. 55-9544
Apr. 28, 1980 [JP] Japan .................................. 55-56455

[51] Int. Cl.³ .................... C07D 253/06; A01N 43/64
[52] U.S. Cl. ..................................... 424/249; 544/182
[58] Field of Search ........................ 544/182; 424/249

[56] References Cited

U.S. PATENT DOCUMENTS

| 3,268,398 | 8/1966 | Kato et al. | 167/33 |
| 4,024,163 | 5/1977 | Elliott et al. | 260/347.4 |
| 4,053,625 | 10/1977 | Ono et al. | 424/274 |
| 4,176,189 | 11/1979 | Itaya et al. | 424/273 |

FOREIGN PATENT DOCUMENTS 2275457 1/1976 France .

*Primary Examiner*—John M. Ford
*Attorney, Agent, or Firm*—Stevens, Davis, Miller & Mosher

[57] ABSTRACT

A carboxylate of the formula,

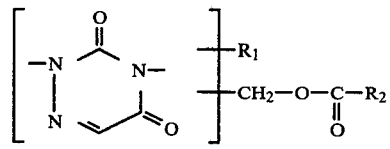

wherein $R_1$ is an allyl or propargyl group, $R_2$ is a group of

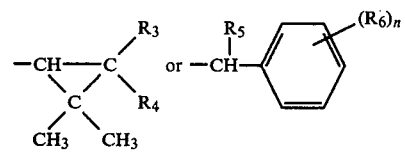

in which $R_3$ is a hydrogen atom or a methyl group, and when $R_3$ is a hydrogen atom, $R_4$ is a group of

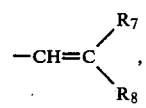

(in which $R_7$ is a chlorine, bromine or fluorine atom, or a methyl, vinyl, methoxycarbonyl or methoxymethyl group, $R_8$ is a hydrogen, chlorine, bromine or fluorine atom or a methyl group), and when $R_3$ is a methyl group, $R_4$ is a methyl group, $R_5$ is an isopropyl or cyclopropyl group, $R_6$ is an alkyl group having 1 to 3 carbon atoms or alkoxy group having 1 to 3 carbon atoms, or a chlorine, bromine or fluorine atom, n is 1 or 2, and —$(R_6)_n$ may include a 3,4-methylenedioxy group, and its use as an insecticide and/or acaricide.

6 Claims, No Drawings

INSECTICIDAL AND ACARICIDAL 3,5-DIOXO-2,3,4,5-TRIAZINE COMPOUNDS

The present invention relates to carboxylic esters of the following formula (I), their production and an insecticide and acaricide containing them as an active ingredient:

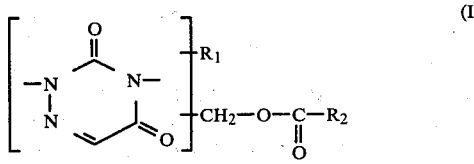

wherein $R_1$ is an allyl or propargyl group, $R_2$ is a group of

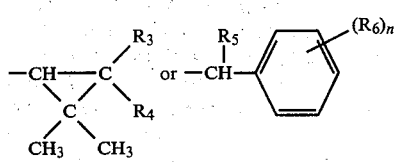

in which $R_3$ is a hydrogen atom or a methyl group, and when $R_3$ is a hydrogen atom, $R_4$ is a group of

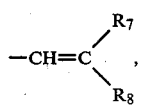

(in which $R_7$ is a chlorine, bromine or fluorine atom, or a methyl, vinyl, methoxycarbonyl or methoxymethyl group, $R_8$ is a hydrogen, chlorine, bromine or fluorine atom or a methyl group, and when $R_3$ is a methyl group, $R_4$ is a methyl group, $R_5$ is an isopropyl or cyclopropyl group, $R_6$ is an alkyl group having 1 to 3 carbon atoms or alkoxyl group having 1 to 3 carbon atoms, or a chlorine, bromine or fluorine atom, n is 1 or 2, and —$(R_6)_n$ may include a 3,4-methylenedioxy group (preferably R is a group of

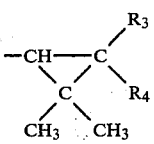

in which $R_3$ is a hydrogen atom or a methyl group, and when $R_3$ is a hydrogen atom, $R_4$ is a group of

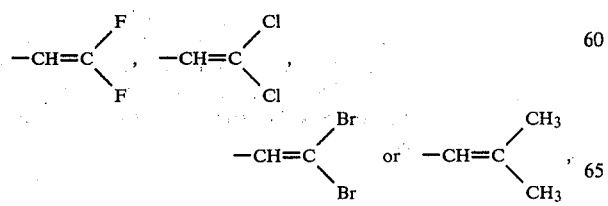

and when $R_3$ is a methyl group, $R_4$ is a methyl group).

What is most important to insect controlling agents is to rapidly knock down and kill insects for preventing the damage.

As a result of a study to develop an insecticide and acaricide having such characteristics, the inventors found that novel carboxylic esters of the formula (I) have excellent knock-down and insecticidal and acaricidal effects against harmful insanitary insects, and confirmed that these compounds can be applied to practical use. The inventors thus completed the present invention.

The present compounds of the formula (I) have very immediate effects against harmful insanitary insects such as flies, mosquitoes and cockroaches. They are also very effective in controlling insects harmful to agricultural crops such as planthoppers, leafhoppers, armyworms and cutworms, diamondback moth (*Plutella xylostella*), tortorixes, aphids and mites, insects harmful to stored cereals such as grain mites, indian meal moth (*Plodia interpunctella*) and rice weevils (*Sitophilus orizae*), and animal-parasitic lice and ticks. Further, they are effective in controlling other insects. The present compounds not only knock down insects to death, but also have repellency to keep insects out of their hosts. They can be applied to practical use in various preparation forms.

Next, the synthetic method for the present compounds will be illustrated.

The ester of the formula (I) is obtained by allowing an alcohol of the formula (II),

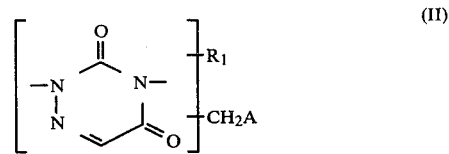

wherein $R_1$ is as defined above and A is a hydroxyl group or a halogen atom such as chlorine or bromine atom, or its halide to react with a carboxylic acid of the formula (III),

wherein $R_2$ is as defined above, or its reactive derivative in the presence of a suitable reaction assistant if necessary. The reactive derivative referred to herein includes acid halides such as acid chloride and acid bromides, (mixed) acid anhydrides, and the salts of the acid with an alkali metal (e.g. sodium, potassium) or organic tertiary base (e.g. trimethylamine, triethylamine).

Next, these methods will be illustrated in more detail.

The first is a method of obtaining the ester of the formula (I) by allowing an alcohol of the formula (IV),

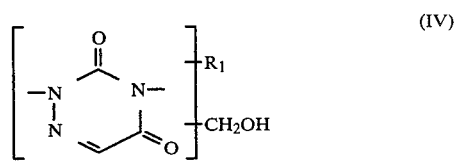

wherein $R_1$ is as defined above, corresponding to an alcohol of the formula (II) wherein A is a hydroxyl group to react with a carboxylic acid of the formula (III) or its acid halide or acid anhydride (mixed acid anhydride).

When the carboxylic acid itself is used, the reaction is achieved under dehydrating conditions. That is, the object can be well achieved by allowing an alcohol of the formula (IV) to react with a carboxylic acid of the formula (III) at a temperature between 0° C. and the boiling point of a solvent used, preferably at room temperature in a solvent such as benzene, toluene, hexane or heptane in the presence of a dehydrating agent such as dicyclohexylcarbodiimide.

When the acid halide is used, the object can be well achieved by allowing it to react with an alcohol of the formula (IV) at a temperature between −20° C. and the boiling point of a solvent used, preferably at room temperature using an acid-binding agent (e.g. pyridine, triethylamine, trimethylamine) as reaction assistant. The acid halide may be any one of those within the scope of this invention, but generally it is an acid chloride. In this reaction, the use of a solvent is not essential, but inert solvents are favorable to allow the reaction to proceed smoothly. Benzene, toluene, dichloromethane or petroleum benzine is generally used as the solvent.

When the acid anhydride is used, the object can be achieved by allowing it to react with an alcohol of the formula (IV) at a temperature between 0° C. and the boiling point of a solvent used, preferably at room temperature without special use of a reaction assistant. Heating, solvents and organic tertiary bases are not essential, although the former one is favorable to promote the reaction, and the latter two are favorable to allow the reaction to proceed smoothly. The bases include for example triethylamine and trimethylamine.

The second is a method of obtaining the ester of the formula (I) by allowing a halide of the formula (V),

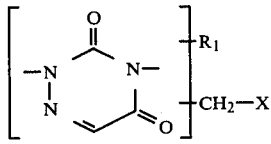

(V)

wherein $R_1$ is as defined above, and X is a halogen atom such as chlorine or bromine atom, corresponding to a compound of the formula (II) wherein A is a halogen atom (e.g. chlorine, bromine) to react with a carboxylic acid of the formula (III). The carboxylic acid may be used as a salt with an alkali metal (e.g. sodium, potassium) or organic tertiary base (e.g. triethylamine, trimethylamine), or may be added to the reaction system together with the alkali metal or organic tertiary base.

For carrying out the reaction by this method, it is desirable to use solvents (e.g. benzene, acetone) and to heat the system to the boiling point of the solvent or less, although the reaction can slowly be achieved at around room temperature.

The group, X, in the formula (V) is generally a chlorine atom, but other halogen atoms may be used. The halides of the formula (V) are easily obtained by the halogenation of the alcohols of the formula (IV).

Next, examples of synthesis will be illustrated by a standard procedure.

A. Reaction between alcohol and carboxylic acid halide

An alcohol (0.05 mole) is added to 3 times its volume of dry dichloromethane, and pyridine (0.075 mole) is added thereto. A carboxylic acid chloride (0.053 mole) is dissolved in 3 times its volume of dry dichloromethane, and added at a time to the above solution at which time exothermic reaction begins. After allowing to stand overnight in air-tight condition, a little water is added to dissolve deposited pyridine hydrochloride, and the aqueous layer is separated. The organic layer is successively washed with 5% aqueous hydrochloric acid, sodium hydrogen carbonate-saturated water and then with sodium chloride-saturated water, and dried over anhydrous sodium sulfate. The dichloromethane solution obtained is concentrated and purified by chromatography on silica gel to obtain the objective ester.

B. Dehydration between alcohol and carboxylic acid

An alcohol (0.05 mole) and a carboxylic acid (0.05 mole) are mixed with 3 times their total volume of dichloromethane, and dicyclohexylcarbodiimide (0.08 mole) is added. After allowing to stand overnight in air-tight condition, the solution is heated under reflux for 2 hours to complete the reaction and then cooled. Deposited dicyclohexylurea is filtered, and the same treatment as the standard procedure A is carried out to obtain the objective ester.

C. Reaction between alcohol and carboxylic acid anhydride

An alcohol (0.05 mole) is added to 3 times its volume of dichloromethane, and a carboxylic acid anhydride (0.05 mole), synthesized from a carboxylic acid and acetic anhydride, is added thereto. After heating under reflux for 3 hours, the carboxylic acid as by-product is recovered by vacuum distillation or neutralization with 5% sodium hydroxide. Thereafter, the same treatment as the standard procedure A is carried out to obtain the objective ester.

D. Reaction between alcohol halide and carboxylic acid salt

An alcohol halide (0.05 mole) and a carboxylic acid (0.06 mole) are dissolved in 3 times their total volume of acetone, and a solution of triethylamine (0.08 mole) in 3 times its volume of acetone is gradually added dropwise at 15° to 20° C. with stirring. After completion of the addition, refluxing is carried out for 2 hours to finish the reaction, and after cooling, deposited triethylamine hydrochloride is filtered. Acetone is removed from the filtrate under reduced pressure, and to the residual liquor is added dichloromethane of 3 times its volume. Thereafter, the same treatment as the standard procedure A is carried out to obtain the objective ester.

Typical examples of the present compound will be shown, but this invention is not of course limited to these examples.

For the ester of the formula (I), there exist stereoisomers based on the steric configuration of the carboxylic acid and optical isomers based on the asymmetric carbon atom. All these esters also are included in the scope of this invention.

| Example No. | Compound No. | Structure | Acid moiety | Refractive index | Reaction form | Yield (%) |
|---|---|---|---|---|---|---|
| 1 | (1) | CH≡C—CH₂—N(C=O)—N(CH₂—C=O)—CH₂—O—C(=O)—CH—CH(C(CH₃)₂)—CH=C(Cl)(Cl) | d.l-cis,trans | $n_D^{28.0}$ 1.5388 | A | 90.7 |
| 2 | (2) | CH₂=CH—CH₂—N(C=O)—N(CH₂—C=O)—CH₂—O—C(=O)—CH—CH(C(CH₃)₂)—CH=C(Cl)(Cl) | d.l-cis,trans | $n_D^{26.0}$ 1.5294 | A | 84.4 |
| 3 | (3)-(a) | CH≡C—CH₂—N(C=O)—N(CH₂—C=O)—CH₂—O—C(=O)—CH—CH(C(CH₃)₂)—CH=C(Cl)(Cl) | d.l-cis,trans | $n_D^{21.0}$ 1.5443 | A | 86.1 |
| 4 | (3)-(b) | | d-trans | $n_D^{24.0}$ 1.5430 | A | 88.1 |
| 5 | (4) | CH₂=CH—CH₂—N(C=O)—N(CH₂—C=O)—CH₂—O—C(=O)—CH—CH(C(CH₃)₂)—CH=C(Cl)(Cl) | d.l-cis,trans | $n_D^{23.5}$ 1.5328 | A | 84.3 |
| 6 | (5) | CH≡C—CH₂—N(C=O)—N(CH₂—C=O)—CH₂—O—C(=O)—CH—CH(C(CH₃)₂)—CH=C(F)(F) | d-trans | $n_D^{28.5}$ 1.4972 | A | 93.2 |
| 7 | (6) | CH≡C—CH₂—N(C=O)—N(CH₂—C=O)—CH₂—O—C(=O)—CH—CH(C(CH₃)₂)—CH=C(Br)(Br) | d-cis | $n_D^{25.5}$ 1.5823 | A | 89.1 |
| 8 | (7) | CH₂=CH—CH₂—N(C=O)—N(CH₂—C=O)—CH₂—O—C(=O)—CH—CH(C(CH₃)₂)—CH=C(CH₃)(CH₃) | d-trans | $n_D^{26.0}$ 1.5088 | A | 85.3 |

-continued

| Example No. | Compound No. | Structure | Acid moiety | Refractive index | Reaction form | Yield (%) |
|---|---|---|---|---|---|---|
| 9 | (8) | $CH_2=CH-CH_2-N\underset{O}{\overset{O}{\underset{\|}{\bigcirc}}}N-CH_2-O-C(=O)-CH-CH-CH=CH-CH=CH_2$ with cyclopropane $C(CH_3)_2$ | d,l-trans | $n_D^{28.5}$ 1.5420 | B | 59.5 |
| 10 | (9) | $CH\equiv C-CH_2-N\underset{O}{\overset{O}{\bigcirc}}N-CH_2-O-C(=O)-CH-CH=C(COOCH_3)(CH_3)$ cyclopropane $C(CH_3)_2$ | d-trans | $n_D^{21.0}$ 1.5555 | A | 87.8 |
| 11 | (10) | $CH_2=CH-CH_2-N\underset{O}{\overset{O}{\bigcirc}}N-CH_2-O-C(=O)-CH-CH=C(CH_2-O-CH_3)(CH_3)$ cyclopropane $C(CH_3)_2$ | d-trans | $n_D^{23.5}$ 1.5353 | A | 86.6 |
| 12 | (11) | $CH\equiv C-CH_2-N\underset{O}{\overset{O}{\bigcirc}}N-CH_2-O-C(=O)-C(CH_3)_2-C(CH_3)_2-CH_3$ | | $n_D^{25.0}$ 1.5064 | A | 88.9 |
| 13 | (12) | $CH_2=CH-CH_2-N\underset{O}{\overset{O}{\bigcirc}}N-CH_2-O-C(=O)-C(CH_3)_2-C(CH_3)_2-CH_3$ | | $n_D^{25.0}$ 1.5042 | A | 83.4 |
| 14 | (13) | $CH\equiv C-CH_2-N\underset{O}{\overset{O}{\bigcirc}}N-CH_2-O-C(=O)-C(CH_3)_2-C(CH_3)_2-CH_3$ | | $n_D^{24.5}$ 1.5087 | A | 85.3 |
| 15 | (14) | $CH_2=CH-CH_2-N\underset{O}{\overset{O}{\bigcirc}}N-CH_2-O-C(=O)-C(CH_3)_2-C(CH_3)_2-CH_3$ | | $n_D^{25.0}$ 1.5062 | A | 79.6 |

-continued

| Example No. | Compound No. | Structure | Acid moiety | Refractive index | Reaction form | Yield (%) |
|---|---|---|---|---|---|---|
| 16 | (15) | [structure with 4-chlorophenyl, CH(CH3)2, CH2=CH-CH2-] | | $n_D^{28.5}$ 1.5382 | A | 87.2 |
| 17 | (16) | [structure with 4-chlorophenyl, cyclopropyl, CH≡C-CH2-] | | $n_D^{22.5}$ 1.5457 | A | 92.5 |
| 18 | (17) | [structure with 3,4-dimethoxyphenyl, CH(CH3)2, CH2=CH-CH2-] | | $n_D^{28.0}$ 1.5324 | D | 56.4 |
| 19 | (18) | [structure with 4-methylphenyl, CH(CH3)2, CH≡C-CH2-] | | $n_D^{28.5}$ 1.5304 | A | 90.2 |
| 20 | (19) | [structure with 4-ethoxyphenyl, CH(CH3)2, CH≡C-CH2-] | | $n_D^{29.5}$ 1.5337 | A | 91.4 |
| 21 | (20) | [structure with 3,4-dichlorophenyl, CH(CH3)2, CH2=CH-CH2-] | | $n_D^{27.0}$ 1.5366 | A | 85.0 |
| 22 | (21) | [structure with 4-bromophenyl, CH(CH3)2, CH≡C-CH2-] | | $n_D^{27.0}$ 1.5563 | B | 61.5 |

| Example No. | Compound No. | Structure | Acid moiety | Refractive index | Reaction form | Yield (%) |
|---|---|---|---|---|---|---|
| 23 | (22) | [structure] | d-trans | $n_D^{19.0}$ 1.5384 | A | 88.5 |
| 24 | (23) | [structure] | d-cis | $n_D^{23.5}$ 1.5853 | A | 90.3 |
| 25 | (24) | [structure] | | $n_D^{25.0}$ 1.5343 | C | 73.1 |
| 26 | (25) | [structure] | | $n_D^{25.0}$ 1.5364 | D | 52.8 |
| 27 | (26) | [structure] | | $n_D^{24.0}$ 1.5423 | A | 87.3 |
| 28 | (27) | [structure] | d-trans | $n_D^{25.0}$ 1.5098 | A | 85.2 |
| 29 | (28) | [structure] | d-trans | $n_D^{28.0}$ 1.4978 | A | 88.1 |

-continued

| Example No. | Compound No. | Structure | Acid moiety | Refractive index | Reaction form | Yield (%) |
|---|---|---|---|---|---|---|
| 30 | (29) | CH$_2$=CH—CH$_2$—N(ring)N—CH$_2$—O—C(=O)—CH—CH—CH=CH—CH=CH$_2$ with C(CH$_3$)$_2$ bridge | d,l-trans | n$_D^{24.5}$ 1.5468 | A | 84.7 |
| 31 | (30) | CH≡C—CH$_2$—N(ring)N—CH$_2$OC(=O)—CH—CH=C(CH$_3$)$_2$ with C(CH$_3$)$_2$ | d-cis,trans | n$_D^{23.5}$ 1.5194 | A | 85.2 |
| 32 | (31) | CH≡C—CH$_2$—N(ring)N—CH$_2$OC(=O)—CH—CH=C(CH$_3$)$_2$ with C(CH$_3$)$_2$ | d-cis,trans | n$_D^{23.5}$ 1.5200 | A | 84.7 |

Of the alcohols of the formula (IV) which are the alcohol moieties of the present esters of the formula (I), alcohols of the formula (VI),

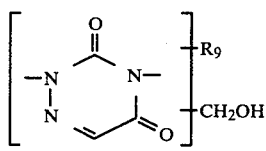
(VI)

wherein R<sub>9</sub> is an allyl or propargyl group, are novel compounds and can be obtained by hydroxymethylation of 3,5-dioxo-2,3,4,5-tetrahydro-1,2,4-triazine derivatives of the formula (VII),

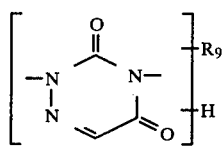
(VII)

wherein R<sub>9</sub> is as defined above. Hydroxymethylating agents used herein include for example formalin, paraformaldehyde and s-trioxane.

When the reaction solvent is water, the pH of the reaction system needs to be made alkaline, preferably 7.5 or more, using basic salts such as alkali metal hydroxides (e.g. sodium hydroxide, potassium hydroxide), trisodium phosphate, disodium hydrogen phosphate, sodium carbonate or potassium carbonate. The reaction temperature is 0° to 70° C., preferably 10° to 60° C., and the reaction time is 30 minutes to 20 hours. The objective compounds can be obtained under such conditions.

When the reaction solvent is dimethylformamide, the hydroxymethylating agent is used in a large excess, the reaction temperature is preferably 100° to 150° C., and the reaction time is 20 minutes to 10 hours. The objective compounds can be obtained under such conditions.

3,5-Dioxo-2,3,4,5-tetrahydro-1,2,4-triazine derivatives of the formula (VII) also are novel compounds and were first synthesized by the inventors. A method of production will be shown below.

Firstly, a compound of the formula (VII) wherein the group R<sub>9</sub> is a substituent linked to the 2-position, that is, 2-substituted-3,5-dioxo-2,3,4,5-tetrahydro-1,2,4-triazine of the formula (VIII),

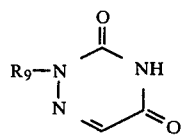
(VIII)

wherein R<sub>9</sub> is as defined above, is obtained by the hydrolysis of 1,2,4-triazine derivatives of the formula (IX) and/or (X),

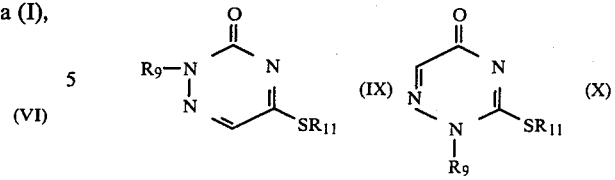

wherein R<sub>9</sub> is as defined above and R<sub>11</sub> is an alkyl having 1 to 5 carbon atoms or a benzyl group. For the hydrolysis, the addition of an acid such as hydrochloric acid, sulfuric acid or nitric acid in addition to water is preferred. Solvents are not always necessary, but water-soluble organic solvents such as alcohols (e.g. methyl alcohol, ethyl alcohol, ethylene glycol), dimethylformamide or dimethyl sulfoxide may be used. The reaction temperature is within a range of 40° to 15° C., preferably 50° to 100° C., and the reaction time is 10 minutes to 10 hours. The objective compounds can be obtained under such conditions.

The 1,2,4-triazine derivatives of the formulae (IX) and/or (X) are novel compounds and can be synthesized by allowing 1,2,4-triazine derivatives of the formulae (XI) and/or (XII),

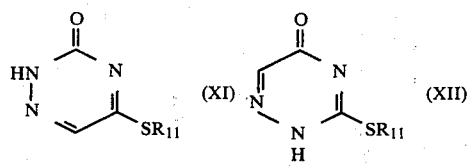

wherein R<sub>11</sub> is as defined above, to react with a halide of the formula (XIII),

wherein R<sub>9</sub> is as defined above and X is a halogen atom such as chloride, bromine or iodine, in the presence of a base. The base includes for example butyl lithium and sodium hydride, and the solvent includes for example ethers (e.g. ether, tetrahydrofuran), and dimethylformamide. The reaction temperature is −70° to 70° C., preferably −50° to 50° C., and the reaction time is 10 minutes to 5 hours. The objective compounds of the formulae (IX) and/or (X) can be obtained under such conditions.

Secondly, a compound of the formula (VII) wherein the group R<sub>9</sub> is a substituent linked to the 4-position, that is, 4-substituted-3,5-dioxo-2,3,4,5-tetrahydro-1,2,4-triazine of the formula (XIV),

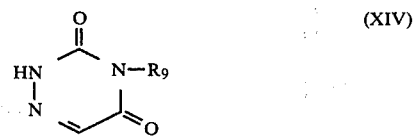
(XIV)

wherein R<sub>9</sub> is as defined above, is obtained by allowing an alkali metal salt of 3,5-dioxo-2,3,4,5-tetrahydro-1,2,4-triazine of the formula (XV),

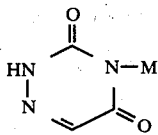

(XV)

wherein M is an alkali metal such as sodium or potassium, to react with a halide of the foregoing formula (XIII).

The solvent used in this reaction includes for example alcohols (e.g. ethyl alcohol, ethylene glycol), dimethylformamide and dimethyl sulfoxide. The reaction temperature is 50° to 200° C., preferably 70° to 150° C., and the reaction time is 1 to 30 hours. The objective compounds can be obtained under such conditions.

Synthetic methods for the compounds of the formulae (VI), (VII), (IX) and (X) will be illustrated in more detail with reference to the following examples and reference examples, which are not however to be interpreted as limiting the invention thereto.

REFERENCE EXAMPLE 1

2-Allyl-3-oxo-5-methylthio-2,3-dihydro-1,2,4-triazine

From 0.42 g of 62.5% sodium hydride diluted with nujol, nujol was removed by washing with n-hexane, and 5 ml dimethylformamide was added thereto. Further, a solution of 1.43 g of 3-oxo-5-methylthio-2,3-dihydro-1,2,4-triazine in 20 ml dimethylformamide was added dropwise over 10 minutes with water cooling. After completion of the addition, stirring was continued for 30 minutes, and 1.57 g allyl bromide was added dropwise over 5 minutes with water cooling. After completion of the addition, stirring was continued for 1 hour. The reaction solution was poured into 80 ml ice water containing 10 ml 10% hydrochloric acid, and the product was extracted with three 60-ml portions of ethyl acetate. The ethyl acetate layer was washed with 20 ml sodium chloride-saturated water and dried over magnesium sulfate. Ethyl acetate was concentrated under reduced pressure to obtain a dark brown liquid. This liquid was purified by chromatography on silica gel using chloroform as solvent to obtain 1.61 g of a pale yellow liquid.

Yield 88.0%

$n_D^{24.5}$ 1.6008

NMR data:

$\delta_{CDCl_3}^{TMS}$ 2.68 (s, 3H), 4.65 (dd, 2H), 5.15 (m, 1H), 5.36 (m, 1H), 5.7–6.3 (m, 1H), 7.4 (s, 1H)

REFERENCE EXAMPLE 2

2-Propargyl-3-methylthio-5-oxo-2,5-dihydro-1,2,4-triazine

To a solution of 1.70 g sodium hydroxide in 50 ml water was added 6.07 g 3-methylthio-5-oxo-2,5-dihydro-1,2,4-triazine at room temperature, followed by stirring for 2 hours. Water was concentrated under reduced pressure and 70 ml ethyl alcohol was added to the residue.

To this solution was added 6.05 g propargyl bromide, followed by 2 hours' heating under reflux. After cooling to room temperature, ethyl alcohol was concentrated under reduced pressure to obtain a black semi-crystal. To the semi-crystal were added 400 ml ethyl acetate and 100 ml water, followed by thorough stirring.

Insoluble matters produced were removed by filtration, and the filtrate was separated into an organic layer and an aqueous layer. The aqueous layer was further extracted with 100 ml ethyl acetate. The ethyl acetate layers were combined, washed with 50 ml water and dried over magnesium sulfate. Ethyl acetate was concentrated under reduced pressure to obtain a black liquid. This liquid was purified by chromatography on silica gel using a n-hexane/ethyl acetate (1:1) mixed solvent to obtain 2.33 g of a pale yellow crystal.

Yield 30.3% m.p. 128°–130° C.

NMR data:

$\delta_{CDCl_3}^{TMS}$ 2.55 (t, 1H), 2.63 (s, 3H), 4.8 (d, 2H), 7.55 (s, 1H)

EXAMPLE 33

2-Allyl-3,5-dioxo-2,3,4,5-tetrahydro-1,2,4-triazine

A mixture of 1.49 g 2-allyl-3-oxo-5-methylthio-2,3-dihydro-1,2,4-triazine, 6 ml conc. hydrochloric acid and 12 ml ethyl alcohol was heated under reflux for 1.5 hours. After cooling to room temperature, the solvent was removed under reduced pressure to obtain a yellow solid. This solid was recrystallized from ethyl alcohol to obtain 1.06 g of a white crystal.

Yield 84.8% m.p. 132.7° C.

NMR data:

$\delta_{CDCl_3-C_2D_6SO}^{TMS}$ 4.47 (dd, 2H), 5.07 (m, 1H), 5.3 (m, 1H), 5.6–7.2 (m, 1H), 7.3 (s, 1H)

EXAMPLE 34

2-Propargyl-3,5-dioxo-2,3,4,5-tetrahydro-1,2,4-triazine

A mixture of 1.34 g 2-propargyl-3-methylthio-5-oxo-2,3-dihydro-1,2,4-triazine, 5 ml conc. hydrochloric acid and 10 ml ethyl alcohol was heated under reflux for 1.5 hours. After cooling to room temperature, the solvent was removed under reduced pressure to obtain a yellow solid. This solid was recrystallized from ethyl alcohol to obtain 0.92 g of a white crystal.

Yield 82.1% m.p. 148.2° C.

NMR data:

$\delta_{CDCl_3}^{TMS}$ 2.4 (t, 1H), 4.8 (d, 1H), 7.53 (s, 1H)

EXAMPLE 35

3,5-Dioxo-4-allyl-2,3,4,5-tetrahydro-1,2,4-triazine

A mixture of 6.12 g 3,5-dioxo-4-sodio-2,3,4,5-tetrahydro-1,2,4-triazine monohydrate, 5.81 g allyl bromide and 50 ml ethylene glycol was heated to 80° C. for 4 hours.

After removing ethylene glycol under reduced pressure, 150 ml ethyl acetate and 30 ml water were added, and after thorough stirring, the solution was separated into an aqueous layer and an ethyl acetate layer. The aqueous layer was further extracted with 100 ml ethyl acetate. The ethyl acetate layers were combined, washed with 20 ml sodium chloride-saturated water and dried over magnesium sulfate. Ethyl acetate was removed under reduced pressure to obtain a pale yellow solid. This solid was recrystallized from ethyl alcohol to obtain 3.52 g of a white crystal.

Yield 57.4% m.p. 154.0° C.

NMR data:

$\delta_{CDCl_3-C_2D_6SO}^{TMS}$ 4.44 (dd, 2H), 5.08 (m, 1H), 5.3 (m, 1H), 5.6–7.3 (m, 1H), 7.32 (s, 1H)

EXAMPLE 36

3,5-Dioxo-4-propargyl-2,3,4,5-tetrahydro-1,2,4-triazine

A mixture of 4.59 g 3,5-dioxo-4-sodio-2,3,4,5-tetrahydro-1,2,4-triazine, 4.64 g propargyl bromide and 40 ml ethylene glycol was heated to 80° C. for 3 hours.

After removing ethylene glycol under reduced pressure, 120 ml ethyl acetate and 25 ml water were added, and after thorough stirring, the solution was separated into an aqueous layer and an ethyl acetate layer. The aqueous layer was further extracted with 80 ml ethyl acetate. The ethyl acetate layers were combined, washed with 20 ml sodium chloride-saturated water and dried over magnesium sulfate. Ethyl acetate was removed under reduced pressure to obtain a dark brown semi-solid. This semi-solid was purified by chromatography on silica gel using chloroform as solvent to obtain a pale yellow crystal. This crystal was recrystallized from an ethyl alcohol/n-hexane (1:1) mixture to obtain 1.94 g of a white crystal.

Yield 46.5% m.p. 93.3° C.

NMR data:

$\delta_{CDCl_3}^{TMS}$ 2.18 (t, 1H), 4.52 (d, 2H), 7.23 (s, 1H)

EXAMPLE 37

2-Hydroxymethyl-3,5-dioxo-4-propargyl-2,3,4,5-tetrahydro-1,2,4-triazine

A mixture of 2.08 g 3,5-dioxo-4-propargyl-2,3,4,5-tetrahydro-1,2,4-triazine, 4.1 ml 35% aqueous formalin, 0.78 g potassium hydroxide and 7 ml water was stirred at 50° C. for 4 hours. After cooling to room temperature, the reaction solution was neutralized to a pH of 7 with acetic acid and extracted with three 30-ml portions of chloroform. The chloroform layers were combined, washed with 10 ml sodium chloride-saturated water and dried over magnesium sulfate. Chloroform was concentrated under reduced pressure to obtain a pale yellow semi-solid.

This semi-solid was purified by chromatography on silica gel using a chloroform/methyl alcohol (50:1) mixed solvent to obtain 0.59 g of a white semi-crystalline product.

Yield 23.6%

NMR data:

$\delta_{CDCl_3}^{TMS}$ 2.26 (t, 1H), 4.62 (d, 2H), 5.37 (s, 2H), 7.43 (s, 1H)

EXAMPLE 38

2-Propargyl-3,5-dioxo-4-hydroxymethyl-2,3,4,5-tetrahydro-1,2,4-triazine

A mixture of 0.76 g 2-propargyl-3,5-dioxo-2,3,4,5-tetrahydro-1,2,4-triazine, 15 ml 37% aqueous formalin and 7.5 ml dimethylformamide was heated under reflux for 1.5 hours. The solvent was removed under reduced pressure to obtain a white semi-solid. This semi-solid was purified by chromatography on silica gel using a chloroform/methyl alcohol (75:1) mixed solvent to obtain 0.61 g of a white semi-crystalline product.

Yield 67.8%

NMR data:

$\delta_{CDCl_3}^{TMS}$ 2.40 (t, 1H), 4.72 (d, 2H), 5.45 (s, 2H), 7.43 (s, 1H)

In the preparation of an insecticide and acaricide from the present compounds of the formula (I), the compounds can be formulated into any preparation form, as in the case of pyrethroid, by the methods well known to those skilled in the art using common diluents for insecticides. As the preparation form, there may be given emulsifiable concentrates, wettable powders, dusts, granules, fine granules, oil sprays, aerosols, heating fumigants (mosquito coils, electric mosquito fumigators), foggings, non-heating fumigants and baits. The compounds can be applied to various uses in required preparation forms and with carriers.

Generally, it is suitable that these preparations contain 0.01 to 95% by weight, preferably 0.05 to 90% by weight, of active ingredients (including other ones mixed). Since, however, the amount and concentration are related to preparation forms, time, technique and place of application, insects to be controlled and crops to be protected, they may be changed optionally.

Further, the insecticidal activity of the present compounds can be increased by mixing with synergists for pyrethroid or other well-known effective synergists for Allethrin or Pyrethrins. The former synergists include for example α[2-(2-butoxyethoxy)-ethoxy]-4,5-methylenedioxy-2-propyltoluene (hereinafter referred to as piperonylbutoxide), 1,2-methylenedioxy-4-[2-(octylsulfinyl)propyl]benzene (hereinafter referred to as sulfoxide), 4-(3,4-methylenedioxyphenyl)-5-methyl-1,3-dioxane (hereinafter referred to as sufroxane), N-(2-ethylhexyl)-bicyclo[2,2,1]hepta-5-ene-2,3-dicarboxiimide (hereinafter referred to as MGK-264), octachlorodipropyl ether (hereinafter referred to as S-421) and isobornyl thiocyanoacetate (hereinafter referred to as Thanite).

In general, chrysanthemate type compounds like the present compounds tend to be inferior in stability to light, heat and oxidation, and therefore compositions of more stable effect can be obtained by adding a proper amount of stabilizers. The stabilizers include for example antioxidants and ultraviolet absorbers such as phenol derivatives (e.g. BHT, BHA), bisphenol derivatives, arylamines (e.g. phenyl-α-naphthylamine, phenyl-β-naphthylamine, condensation products of phenetidine and acetone), and benzophenone compounds.

Further, multi-purpose compositions of excellent efficacy can be produced by mixing with other active ingredients, for example Allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate, 5-propargylfurfuryl chrysanthemate, 2-methyl-5-propargyl-3-furylmethyl chrysanthemate, d-trans or d-cis.trans isomers of these chrysanthemates, pyrethrum extracts, d-trans or d-cis.-trans chrysanthemic ester of d-allethrolone, other well-known cyclopropanecarboxylic esters, organo-phosphorus insecticides such as O,O-dimethyl-O-(3-methyl-4-nitrophenyl)phosphorothioate (hereinafter referred to as Fenitrothion), O,O-dimethyl O-4-cyanophenylphosphorothioate (hereinafter referred to as Cyanophos), O,O-dimethyl O-(2,2-dichlorovinyl)-phosphate (hereinafter referred to as dichlorovos), carbamate insecticides such as 1-naphthyl N-methylcarbamate, 3,4-dimethylphenyl N-methylcarbamate (hereinafter referred to as MPMC), other insecticides, microbial agricultural chemicals such as fungicides, nematocides, acaricides, herbicides, plant growth regulators, fertilizers, BT (Bacillus thuringiensis preparations) and BM (Bacillus moritai preparations), insect hormone compounds and other agricultural chemicals. Further, a synergistic effect can be expected by such mixing.

Next, the preparation and effect of the combined insecticides and acaricides of the present invention will be illustrated with reference to the following preparation examples and test examples.

PREPARATION EXAMPLE 1

0.1 Part of each of the present compounds (1) to (31) is dissolved in kerosene and made up to 100 parts with kerosene. The oil spray of each compound is thus obtained.

PREPARATION EXAMPLE 2

To 0.05 part of each of the present compounds (1), (3), (5) and (9) is added 0.25 part of piperonylbutoxide, and the mixture is dissolved in kerosene and made up to 100 parts with kerosene. The oil spray of each compound is thus obtained.

PREPARATION EXAMPLE 3

To 20 parts of each of the present compounds (1) to (31) are added 10 parts of an emulsifier (Sorpol 3005X, a registered trade mark of Toho Chemical Co.) and 70 parts of xylene. The mixture is well mixed with stirring to obtain the emulsifiable concentrate of each compound.

PREPARATION EXAMPLE 4

To 10 parts of each of the present compounds (1), (2), (8) and (17) are added 20 parts of S-421 (described above), 10 parts of an emulsifier (Sorpol 3005X, described above) and 60 parts of xylene. The mixture is well mixed with stirring to obtain the emulsifiable concentrate of each compound.

PREPARATION EXAMPLE 5

0.1 Part of the present compound (31), 0.2 part of resmethrin (described above), 7 parts of xylene and 7.7 parts of deodorized kerosene are well mixed to make a solution. The solution is filled in an aerosol container. After attaching a valve portion to the container, 85 parts of a propellant (liquefied petroleum gas) is charged therein under pressure through the valve to obtain an aerosol.

PREPARATION EXAMPLE 6

0.1 Part of the present compound (30), 0.1 part of tetramethrin (described above), 0.2 part of resmethrin (described above), 7 parts of xylene and 7.6 parts of deodorized kerosene are well mixed to make a solution. The solution is filled in an aerosol container. After attaching a valve portion to the container, 85 parts of a propellant (liquefied petroleum gas) is charged therein under pressure through the valve to obtain an aerosol.

PREPARATION EXAMPLE 7

0.2 Part of the present compound (1), 0.1 part of d-trans isomer of Allethrin, 0.3 part of Fenitrothion (described above), 11.4 parts of deodorized kerosene and 1 part of an emulsifier (Atoms 300, a registered trade mark of Atlas Chemical Co.) are mixed and emulsified with addition of 50 parts of distilled water. The emulsion is then filled in an aerosol container together with 37 parts of a 3:1 mixture of deodorized butane and deodorized propane to obtain a water-based aerosol.

PREPARATION EXAMPLE 8

To 0.6 g of the present compound (13) is added 0.4 g BHT, and the mixture is dissolved in 20 ml of methanol. This solution and 99 g of a mosquito coil carrier containing Tabu powder, Pyrethrum marc and wood powder in a ratio of 3:5:1 are uniformly mixed with stirring, and then methanol is evaporated. To the residue is added 150 ml of water, and the mixture is well kneaded, shaped and dried to obtain a mosquito coil.

PREPARATION EXAMPLE 9

To 0.3 g of each of the present compounds (2), (11) and (12) is added 0.3 g of the d-trans chrysanthemic ester of Allethrin, and the mixture is dissolved in 20 ml of methanol. This solution and 99.4 g of a mosquito coil carrier (described above) are uniformly mixed with stirring, and then methanol is evaporated. To the residue is added 150 ml of water, and the mixture is well kneaded, shaped and dried to obtain the mosquito coil of each compound.

PREPARATION EXAMPLE 10

To 0.1 g of the present compound (13) are added 0.05 g of 5-propargylfurfuryl dl-cis.trans-chrysanthemate and 0.1 g of BHT, and the mixture is dissolved in a suitable amount of chloroform.

The solution is allowed to uniformly permeate a filter paper of 3.5 cm × 1.5 cm × 0.3 cm (thick) to obtain a fibrous fumigant for heating on a hot plate.

PREPARATION EXAMPLE 11

To 20 parts of each of the present compounds (1), (4) and (9) are added 20 parts of Fenitrothion (described above) and 5 parts of an emulsifier (Sorpol 5029-0, a registered trade mark of Toho Chemical Co.), followed by thorough mixing. The mixture is then well mixed with 55 parts of 300-mesh diatomaceous earth while being stirred in a mortar to obtain the wettable powder of each compound.

PREPARATION EXAMPLE 12

To 0.2 part of each of the present compounds (16) and (21) is added 2 parts of 2-sec-butylphenyl N-methylcarbamate, and the mixture is dissolved in 20 parts of acetone. The solution is then well mixed with 97.8 parts of 300-mesh talc while being stirred in a mortar, and acetone is then removed by evaporation to obtain the dust of each compound.

PREPARATION EXAMPLE 13

To 3 parts of each of the present compounds (1), (12) and (19) are added 5 parts of Toyolignin CT (a registered trade mark of Toyo Spinning Co.) and 92 parts of GSM Clay (a registered trade mark of Zieklite Mining Co.), and the mixture is well mixed while being stirred in a mortar.

To the mixture is then added water of 10% based thereon, and after thorough mixing, it is granulated by means of a granulator and air-dried to obtain the granule of each compound.

PREPARATION EXAMPLE 14

To 2 parts of each of the present compounds (2), (10) and (15) are added 2 parts of Cyanox (described above), 5 parts of Toyolignin CT (described above) and 91 parts of GSM Clay (described above), and the mixture is well mixed while being stirred in a mortar.

To the mixture is then added water of 10% based thereon, and after thorough mixing, it is granulated by means of a granulator and air-dried to obtain the fine granule of each compound.

TEST EXAMPLE 1

Ten German cockroach adults (*Blattella germanica*) were liberated in a glass Petri dish of 10 cm in diameter of which the inside wall was coated with a thin layer of vaseline, and the dish was covered with 50-mesh nylon gauze. Thereafter, the 0.6 ml of the 0.1% oil spray obtained in Preparation example 1 was sprayed at a point 50 cm apart therefrom by means of a glass atomizer with a 0.1% oil spray of Allethrin as a control. After 10 minutes, the number of knocked-down insects was counted.

| Test compound | Knock-down ratio after 10 minutes (%) | Test compound | Knock-down ratio after 10 minutes (%) |
|---|---|---|---|
| (1) | 100 | (2) | 100 |
| (3)-(a) | 100 | (4) | 100 |
| (5) | 100 | (6) | 100 |
| (7) | 100 | (8) | 95 |
| (9) | 100 | (10) | 100 |
| (11) | 100 | (12) | 85 |
| (13) | 100 | (14) | 95 |
| (15) | 80 | (16) | 100 |
| (17) | 80 | (18) | 90 |
| (19) | 75 | (20) | 80 |
| (21) | 65 | (22) | 100 |
| (23) | 100 | (24) | 80 |
| (25) | 100 | (26) | 90 |
| (27) | 100 | (28) | 100 |
| (29) | 90 | (30) | 100 |
| (31) | 100 | | |
| Allethrin | 40 | No treatment | 0 |

TEST EXAMPLE 2

Ten female adults of northern house mosquito (*Culex pipiens pallens*) were liberated in a (70 cm)$^3$ glass chamber, and 0.7 ml of the 0.1% oil spray obtained in Preparation example 1 was sprayed. After spraying, the number of knocked-down insects was counted with the lapse of time, and from the results, $KT_{50}$ (period of time required for 50% of insects to be knocked down) was calculated.

| Test compound | $KT_{50}$ (sec) |
|---|---|
| (1) | 49 |
| (2) | 75 |
| (3)-(a) | 42 |
| (3)-(b) | <38 |
| (4) | 80 |
| (5) | <38 |
| (6) | 46 |
| (7) | 75 |
| (9) | 39 |
| (10) | 50 |
| (11) | 56 |
| (13) | 58 |
| (16) | 86 |
| (17) | 100 |
| (22) | 54 |
| (23) | 49 |
| (25) | 90 |
| (28) | <38 |
| (29) | 55 |
| (30) | 48 |
| (31) | 50 |
| Tetramethrin | 130 |
| Pyrethrin | 310 |

TEST EXAMPLE 3

Five milliliters of the oil spray obtained in Preparation example 2 was sprayed on about 100 housefly adults (*Musca domestica*) per group, according to the Campbell's turntable method [Soap and Sanitary Chemicals, Vol. 14, No. 6, 119 (1938)]. The adults were thus exposed to the descending mist for 10 minutes. By the next day, more than 80% of the houseflies could be killed in each case.

TEST EXAMPLE 4

The insecticidal activity on housefly adults (*Musca domestica*) of the aerosols obtained in Preparation examples 5, 6 and 7 was tested according to the aerosol test method (Soap and Chemical Specialities, Blue Book, 1965) using a (6 ft)$^3$ Peet Grady's Chamber. As a result, with any aerosol, more than 80% of the flies could be knocked down 15 minutes after spraying, and more than 70% of the flies could be killed by the next day.

TEST EXAMPLE 5

About 50 female adults of northern house mosquito (*Culex pipiens pallens*) were liberated in a (70 cm)$^3$ glass chamber in which a battery-type small electric fan (wing diameter, 13 cm) was placed and driven.

0.1 Gram of the mosquito coil obtained in Preparation examples 8 and 9 was ignited at one end and placed at the center of the bottom of the chamber. With any mosquito coil, more than 90% of the mosquitoes could be knocked down within 20 minutes, and more than 80% of the mosquitoes could be killed by the next day.

TEST EXAMPLE 6

About 20 rice seedlings were grown up to a 3- to 4-leaf stage in a flower pot (diameter 10 cm), and the dust obtained in Preparation example 12 was applied at a rate of 3 kg/10 are by means of a Bell jar duster. After application, the pot was covered with a wire-screen net, and 20 to 30 green rice leaf-hopper adults (*Nephotettix cincticeps*) were liberated therein. The dead and alive after 24 hours were observed, and as a result, the mortality was more than 80% in each case.

TEST EXAMPLE 7

Carmine mite female adults (*Tetranychus cinnabarinus*) were made parasitic on the leaves of potted kidney bean in the primary leaf stage, at a rate of 10-15-/leaf, which had elapsed 9 days after sowing, and bred at 27° C. in a constant temperature room. After one week, numerous carmine mites in various growth stages were found. At this time, a 200-fold aqueous dilute liquor of each of the emulsifiable concentrates of the present compounds (2), (5), (6), (11), (13), (14) and (28) obtained in Preparation example 3 was sprayed at a rate of 10 ml/pot by means of a turntable. Ten days after spraying, the degree of damage of kidney bean was examined, but little damage was observed in each case.

As is clear from the above-stated efficacy results, all the compounds of the present invention are excellent in effects compared with the reference compounds, particularly in knock-down effect.

Among the compounds of the present invention, the compounds particularly excellent in effect are those having the formula (I) wherein $R_2$ is a group of

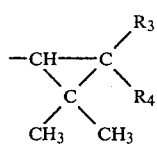

in which $R_3$ is a hydrogen atom or a methyl group, and when $R_3$ is a hydrogen atom, $R_4$ is a group of

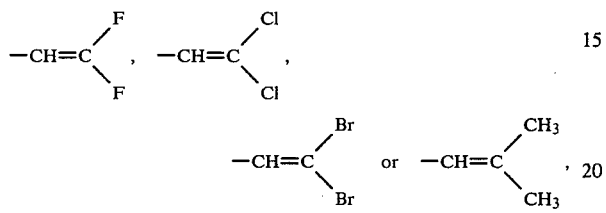

and when $R_3$ is a methyl group, $R_4$ is a methyl group; and further much more excellent when $R_1$ is a propargyl group.

What is claimed is:

1. A carboxylate of the formula,

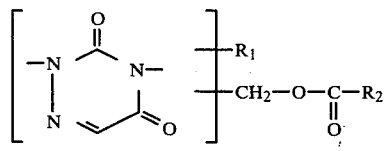

wherein $R_1$ is an allyl or propargyl group, $R_2$ is a group of

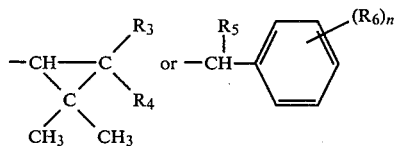

in which $R_3$ is a hydrogen atom or a methyl group, and when $R_3$ is a hydrogen atom, $R_4$ is a group of

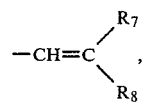

(in which $R_7$ is a chlorine, bromine or fluorine atom, or a methyl, vinyl, methoxycarbonyl or methoxymethyl group, $R_8$ is a hydrogen, chlorine, bromine or fluorine atom or a methyl group), and when $R_3$ is a methyl group, $R_4$ is a methyl group, $R_5$ is an isopropyl or cyclopropyl group, $R_6$ is an alkyl group having 1 to 3 carbon atoms or alkoxyl group having 1 to 3 carbon atoms, or a chlorine, bromine or fluorine atom, n is 1 to 2, and —$(R_6)_n$ may include a 3,4-methylenedioxy group.

2. The compound according to claim 1, wherein $R_2$ is a group of

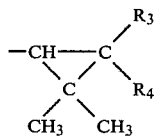

in which $R_3$ is a hydrogen atom or a methyl group, and when $R_3$ is a hydrogen atom, $R_4$ is a group of

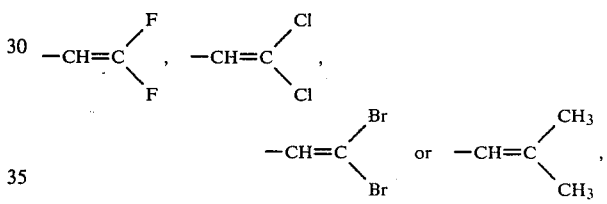

and when $R_3$ is a methyl group, $R_4$ is a methyl group.

3. 3,5-Dioxo-2-propargyl-2,3,4,5-tetrahydro-1,2,4-triazine-4-methyl 2,2-dimethyl-3-(2,2-dichlorovinyl)cyclopropanecarboxylate.

4. 3,5-Dioxo-4-propargyl-2,3,4,5-tetrahydro-1,2,4-triazine-2-methyl 2,2-dimethyl-3-(2,2-dichlorovinyl)cyclopropanecarboxylate.

5. An insecticidal and/or acaricidal composition which comprises as an active ingredient an insecticidally and/or acaricidally effective amount of the compound according to claim 1 and an inert carrier.

6. A method for controlling an insect and/or acarid, which comprises applying an insecticidally and/or acaricidally effective amount of the compound according to claim 1 to the insect and/or acarid.

* * * * *